(12) United States Patent
Choi et al.

(10) Patent No.: US 11,034,586 B2
(45) Date of Patent: Jun. 15, 2021

(54) METHOD OF PREPARING HYDROPHOBIC POROUS SILICA AND HYDROPHOBIC POROUS SILICA

(71) Applicant: Research & Business Foundation Sungkyunkwan University, Suwon-si (KR)

(72) Inventors: Jae Young Choi, Suwon-si (KR); Su Dong Chae, Suwon-si (KR); Jang Ho Park, Suwon-si (KR); Sung Ho Lee, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/553,482

(22) Filed: Aug. 28, 2019

(65) Prior Publication Data

US 2019/0389732 A1    Dec. 26, 2019

Related U.S. Application Data

(63) Continuation of application No. PCT/KR2017/008924, filed on Aug. 17, 2017.

(30) Foreign Application Priority Data

Mar. 31, 2017  (KR) .......................... 10-2017-0041572

(51) Int. Cl.
    *C01B 33/18*  (2006.01)
    *A61K 8/02*  (2006.01)
    (Continued)

(52) U.S. Cl.
    CPC ............ *C01B 33/18* (2013.01); *A61K 8/0279* (2013.01); *A61K 8/585* (2013.01); *A61Q 19/10* (2013.01); *A61K 2800/28* (2013.01)

(58) Field of Classification Search
    CPC ...... C01B 33/18; A61K 8/0279; A61K 8/585; A61K 2800/28; A61K 8/25; A61Q 19/10; A61Q 19/00
    See application file for complete search history.

(56) References Cited

U.S. PATENT DOCUMENTS

| | | | | |
|---|---|---|---|---|
| 3,024,126 A | * | 3/1962 | Brown | C04B 35/14 |
| | | | | 106/490 |
| 3,635,743 A | * | 1/1972 | Smith | C01B 33/113 |
| | | | | 106/490 |
| 5,708,069 A | * | 1/1998 | Burns | C08K 9/06 |
| | | | | 427/219 |

FOREIGN PATENT DOCUMENTS

| | | |
|---|---|---|
| JP | H08-119619 A | 5/1996 |
| JP | 2009-120416 A | 6/2009 |

(Continued)

OTHER PUBLICATIONS

International Search Report dated Dec. 18, 2017 in counterpart International Patent Application No. PCT/KR2017/008924 (2 pages in English and 2 pages in Korean).

(Continued)

*Primary Examiner* — Anthony J Zimmer
(74) *Attorney, Agent, or Firm* — NSIP Law

(57) ABSTRACT

A method of preparing hydrophobic porous silica includes reacting a porous silica particle containing a hydrophilic group in a solvent with an organosilane compound under a basic catalyst to form a mixture, drying the mixture comprising the porous silica particle in a vacuum, and condensation reacting the hydrophilic group of the porous silica particle with the organosilane compound on the surface of the porous silica particle to modify the surface of the porous silica particle to be hydrophobic.

9 Claims, 4 Drawing Sheets

(51) Int. Cl.
  *A61K 8/58*  (2006.01)
  *A61Q 19/10*  (2006.01)

(56) References Cited

FOREIGN PATENT DOCUMENTS

| | | | |
|---|---|---|---|
| JP | 2011-088832 A | | 5/2011 |
| JP | 2011088832 A | * | 5/2011 |
| KR | 10-2012-0033159 A | | 4/2012 |
| KR | 10-2012-0105872 A | | 9/2012 |
| KR | 10-1350843 B1 | | 1/2014 |
| KR | 10-1416053 B1 | | 7/2014 |

OTHER PUBLICATIONS

Korean Office Action dated Oct. 19, 2017 in corresponding Korean Application No. 10-2017-0041572 (6 pages in Korean).

* cited by examiner

METHOD OF PREPARING HYDROPHOBIC POROUS SILICA AND HYDROPHOBIC POROUS SILICA

CROSS-REFERENCE TO RELATED APPLICATIONS

This application is a continuation of International Application No. PCT/KR2017/008924 filed on Aug. 17, 2017, which claims the benefit of Korean Patent Application No. 10-2017-0041572 filed on Mar. 31, 2017, in the Korean Intellectual Property Office, the entire disclosures of which are incorporated herein by reference for all purposes.

BACKGROUND

1. Field

The present disclosure relates to a method of preparing a porous silica particle having a hydrophobically modified surface, to a hydrophobic porous silica particle thus prepared in which at least 90% of the surface area has been modified hydrophobically, and to a hydrophobic porous silica particle having 90% or more of the surface area being hydrophobic.

2. Description of the Background

In general, the skin consists of three layers of epidermis, dermis and subcutaneous fat tissue in order from the outside. The skin is a very important tissue that not only protects the human body in direct contact with the external environment but also has biochemical and physical functions.

The skin is covered with sebum, sweat, dust, old dead skin cells, and the like, and thus, may cause acne and seborrheic dermatitis. Thus, cosmetics for removing sebum, sweat, dust, old dead skin cells, and the like are needed.

The cosmetics for removing dead skin cells may be applied to the skin for use. The cosmetics may have a face-washing effect for effectively removing skin metabolism harmful substances, secretions, contaminants adhered from the outside, bacteria, make-up residue materials and the like; a massage effect for stimulating the nerves and blood vessels distributed in the dermis and subcutaneous tissues of the skin to function to promote blood flow, thereby preventing fine lines; and a peeling effect for preventing the thickening of the stratum corneum by making it possible to easily remove the keratinized keratin so as to keep the skin healthy and fresh.

Accordingly, many studies have been conducted on the exfoliating cosmetics which do not cause skin damage and which can maintain moisture after exfoliation, and as a result, exfoliating cosmetics such as Korean Patent No. 10-1350843 or 10-1416053 have been developed.

Meanwhile, when particles used for the exfoliation cosmetics absorb the moisture of the skin quickly, the user feels dry. Therefore, the porous particles used in the exfoliation cosmetics need to have hydrophobicity so that they can quickly absorb only the oil without absorbing the moisture.

However, the particles mainly used in conventional exfoliating cosmetics are made of plastic microbeads, and these microbeads have a problem that they are not decomposed because they have persistence. Therefore, the microbeads used for exfoliating cosmetics may be introduced into seawater, accumulated in marine organisms, and returned to humans through the food chain. Further, the microbeads may flow in the ocean and absorb various substances, resulting in a sharp increase in toxicity.

Therefore, porous silica particles have been in the spotlight as an alternative to the microbeads. However, since the surfaces of general porous silica particles mainly consist of Si—OH bonds, they have hydrophilic properties.

In order for the porous silica particles to absorb the oil and have hydrophobicity at the same time, it is necessary to develop a technique of coating the surfaces of the outer wall of the pores uniformly and thinly to be hydrophobic without blocking the pores of the particles.

The above information is presented as background information only to assist with an understanding of the present disclosure. No determination has been made, and no assertion is made, as to whether any of the above might be applicable as prior art with regard to the disclosure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a first aspect of the present disclosure a method of preparing hydrophobic porous silica includes reacting a porous silica particle including a hydrophilic group in a solvent with an organosilane compound under a basic catalyst to form a mixture, drying the mixture including the porous silica particle in a vacuum, and condensation reacting the hydrophilic group of the porous silica particle with the organosilane compound on the surface of the porous silica particle to modify the surface of the porous silica particle to be hydrophobic.

According to an embodiment of the present disclosure, the organosilane compound may be hydrolyzed in the solvent, but is not limited thereto.

According to an embodiment of the present disclosure, the organosilane compound may include, but is not limited to, a compound represented by the following Chemical Formula 1:

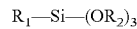

$$R_1\text{—}Si\text{—}(OR_2)_3 \qquad \text{[Chemical Formula 1]}$$

Here, $R_1$ may be an alkyl group having C1 to C12, an alkenyl group having C2 to C10, a cycloalkyl group having C3 to C12 or an aryl group having C6 to C12, and $R_2$ may be an alkyl group having C1 to C6.

According to an embodiment of the present disclosure, the method may further include, after the step of reacting the porous silica particle containing a hydrophilic group with an organosilane compound under the basic catalyst, adding an acidic solution to adjust the pH of the solution, but is not limited thereto.

According to an embodiment of the present disclosure, the step of drying the porous silica particle in a vacuum may be carried out at 70° C. to 150° C., but is not limited thereto.

According to an embodiment of the present disclosure, the solvent may be one selected from the group consisting of distilled water, ethanol, methanol, isopropyl alcohol, n-propyl alcohol, butanol, and combinations thereof, but is not limited thereto.

According to an embodiment of the present disclosure, the basic catalyst may be ammonia water ($NH_4OH$), but is not limited thereto.

According to an embodiment of the present disclosure, the pH of the mixed solution may be adjusted to pH 10 to pH 14 by the basic catalyst, but is not limited thereto.

According to an embodiment of the present disclosure, the acidic solution may be one selected from the group consisting of HCl, $H_2SO_4$, $HNO_3$ and combinations thereof, but is not limited thereto.

According to an embodiment of the present disclosure, the step of adding the acidic solution to adjust the pH of the solvent is such that the pH of the solvent may be adjusted to a pH 5 to pH 8, but is not limited thereto.

According to an embodiment of the present disclosure, a hydrophobic porous silica particle may be prepared by the method, wherein at least 90% of the surface area of the porous silica particle is modified to be hydrophobic.

In a second aspect of the present disclosure, a hydrophobic porous silica particle includes a porous silica particle having a hydrophobic layer disposed on 90% or more of the surface area of the porous silica particle.

The surface area of the porous silica particle may include surface area of inner pores.

The hydrophobic layer may include reaction product of organosilane compound and hydrophilic group bonded to the porous silica particle surface.

The above-described technical solutions are merely exemplary and should not be construed as limiting the present disclosure. In addition to the exemplary embodiments described above, there may be additional embodiments in the drawings, the detailed description of the disclosure, and the claims.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION

Figure 1:
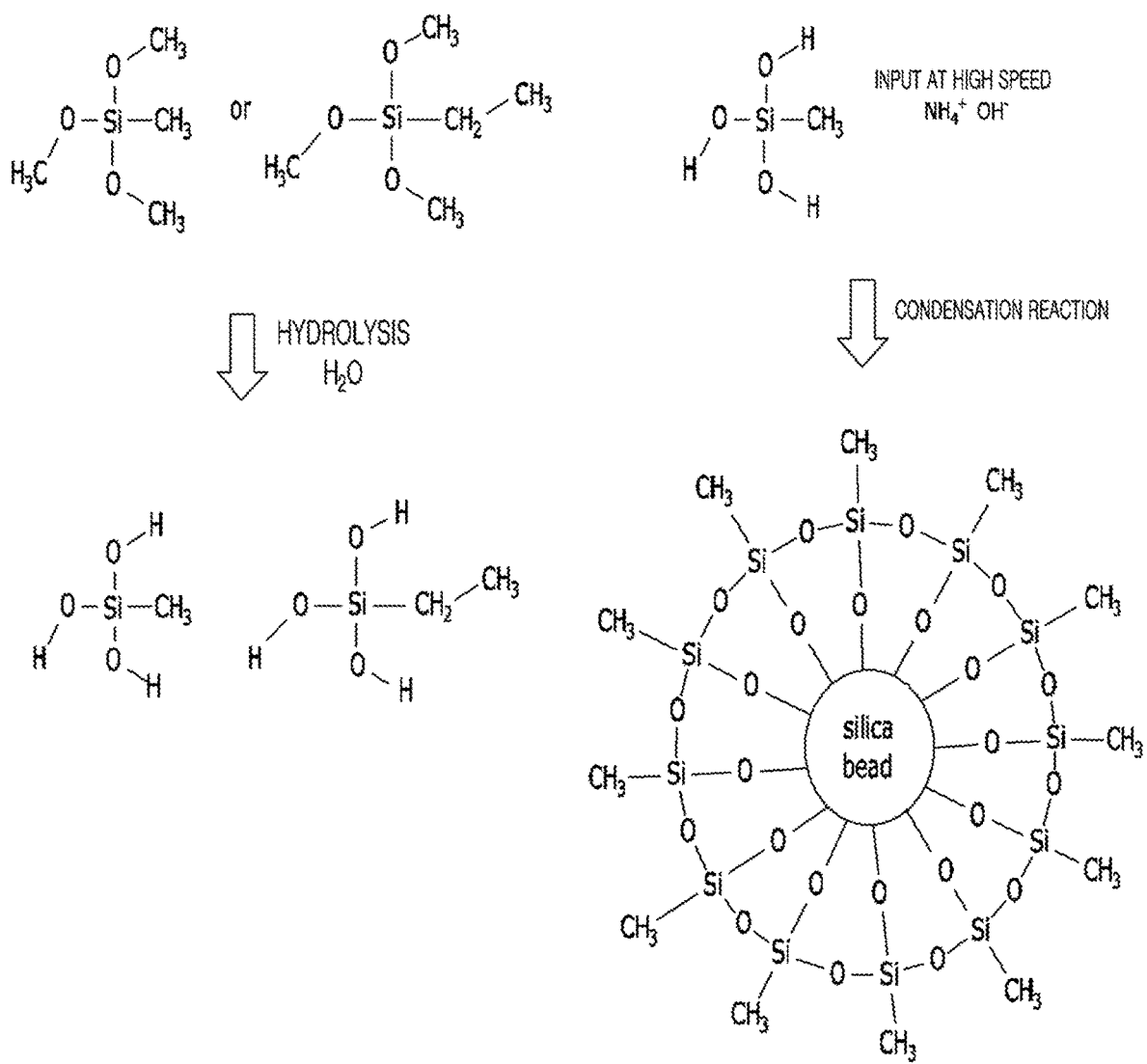
FIG. 1 is a schematic diagram showing that the surface of silica is polymerized with an OH group of the hydrolyzed organosilane compound, thereby modifying Si—OH of the surface to the hydrophobicity of Si—O—R, according to an embodiment of the present disclosure.

Hereinafter, the embodiments of the present disclosure will be described in detail with reference to accompanying drawings so that the embodiments may be easily implemented by those skilled in the art.

However, the present disclosure may be implemented in various ways without being limited to the embodiments. In addition, in the drawings, well-known elements or components may be omitted to avoid unnecessarily obscuring the presented embodiments, and like reference numerals denote like elements throughout the specification.

In the present disclosure, the term "connected to" or "coupled to" that is used to designate a connection or coupling of one element to another element includes both a case that an element is "directly connected or coupled to" another element and a case that an element is "electronically connected or coupled to" another element via still another element.

In the present disclosure, the term "on", "above", "upper", "under", "below", "bottom" that is used to designate a position of one element with respect to another element includes both a case that the one element is adjacent to another element and a case that any other element exists between these two elements.

In the present disclosure, when any portion "includes" any component, this does not exclude other components but means that any other component can be further included, unless stated otherwise.

In the present disclosure, the term representing the degree such as "about" and "substantially" means that any value is identical or close to a suggested numeral when an inherent fabrication error is proposed, and this is used for preventing any unscrupulous infringer from unfairly using the disclosure containing an exact or absolute numeral, which is mentioned for better understanding of the present disclosure. Further, in the entire specification of the present disclosure, a "step . . . " or a "step of . . . " does not mean a "step for . . . ."

In the present disclosure, the term "combination thereof" included in Markush-type expressions refers to a mixture or combination of one or more selected from the group consisting of components described by a Markush-type expression, and one or more selected from the group consisting of the components.

In the present disclosure, the description of "A and/or B" means "A, B, or A and B."

Herein, it is noted that use of the term "may" with respect to an example, for example, as to what an example may include or implement, means that at least one example exists in which such a feature is included or implemented while all examples are not limited thereto.

An object of the present disclosure is to provide a method for producing porous silica particles whose surface has been modified to be hydrophobic.

Another object of the present disclosure is to provide a hydrophobic porous silica particle prepared by the above-mentioned production method.

It should be understood, however, that the technical scope of the embodiments of the present disclosure is not limited to the above-described technical issues, but may include other technical issues.

According to the solution of the present disclosure as described above, the present disclosure may provide a method of preparing hydrophobic porous silica, which is capable of modifying the surface of the porous silica to have a hydrophobic property, and hydrophobic porous silica produced thereby.

In the manufacturing method of the present disclosure, using a basic catalyst, the surface of the silica particles is modified from Si—OH to Si—O—R by polymerizing the OH group of the hydrolyzed organosilane compound with the surface of the porous silica particles containing a hydrophilic group, thereby preparing hydrophobic porous silica in which 90% or more of the surface is modified to be hydrophobic.

The hydrophobic porous silica according to the present disclosure has 90% or more of the porous surface having hydrophobicity, thereby increasing the water repellency and oil absorption so that the hydrophobic porous silica can be usefully applied to exfoliation cosmetics.

Hereinafter, a method of producing porous silica particles having a hydrophobically modified surface and hydrophobic porous silica particles produced by the method according to the present disclosure are described in detail with reference to embodiments, examples, and drawings. However, the present disclosure is not limited to these embodiments, examples and drawings.

The first aspect of the present disclosure relates to a method of preparing hydrophobic porous silica, in which the method includes reacting a porous silica particle containing a hydrophilic group in a solvent with an organosilane compound under a basic catalyst to make a mixture, and drying the mixture including the porous silica particle in a vacuum, and condensation reacting the hydrophilic group of the porous silica particle with the organosilane compound on the surface of the porous silica particle to modify the surface of the porous silica particle to be hydrophobic.

The method of preparing hydrophobic porous silica according to the present disclosure allows polymerization of the surface of the porous silica particle containing a hydrophilic group with the OH group of the hydrolyzed organosilane compound using a basic catalyst, thereby modifying the surface of the silica particles from a Si—OH to the Si—O—R (here, R represents a hydrophobic group contained in the organosilane compound). This makes it possible to produce hydrophobic porous silica in which 90% or more of the surface including pores is modified to be hydrophobic. The hydrophobic porous silica has improved water repellency and oil absorption, and thus can be usefully used in exfoliation cosmetics.

Particularly, the porous silica particle is dried in a vacuum so that 90% or more of the surface area including the pores of the porous silica particle can be uniformly coated with a hydrophobic molecule.

The solvent may be one selected from the group consisting of distilled water, ethanol, methanol, isopropyl alcohol, n-propyl alcohol, butanol, and combinations thereof, and more preferably, it may be a mixture of distilled water and ethanol, but is not limited thereto.

According to an embodiment of the present disclosure, the organosilane compound may be hydrolyzed in the solvent, but is not limited thereto.

According to an embodiment of the present disclosure, the organosilane compound may, but is not limited to, including the compound represented by the following chemical formula 1:

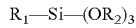   [Chemical Formula 1]

Here, $R_1$ may be an alkyl group having C1 to C12, an alkenyl group having C2 to C10, a cycloalkyl group having C3 to C12 or an aryl group having C6 to C12, and $R_2$ may be an alkyl group having C1 to C6.

The alkyl group, alkenyl group, aryl group and acyl group may all be substituted. The carbon number of the alkyl group, alkenyl group, aryl group and acyl group does not include the number of carbon atoms contained in the substituent group. Specific examples of the alkyl group and the substituent thereof may include a methyl group, an ethyl group, an n-propyl group, an isopropyl group, an n-butyl group, a t-butyl group, a n-hexyl group, a n-decyl group, a trifluoromethyl group, 3,3,3-trifluoropropyl group, 3-glycidoxypropyl group, 2-(3,4-epoxycyclohexyl) ethyl group, [(3-ethyl-3-oxetanyl) methoxy] propyl group, 3-aminopropyl group, 3-mercaptopropyl group, 3-isocyanate propyl group and the like. Specific examples of the alkenyl group and substituent thereof may include a vinyl group and the like. Specific examples of the aryl group and substituent thereof may include a phenyl group, a tolyl group, a p-hydroxyphenyl group, a condensed polycyclic aromatic hydrocarbon group such as a naphthyl group, a phenanthrenyl group, a fluorenyl group, a pyrenyl group, an indenyl group, an acenaphthenyl group and the like. Specific examples of the acyl group and the substituent thereof may include an acetyl group and the like.

The organosilane compound represented by Chemical Formula 1 as described above may be one selected from the group consisting of silanes with quaternary functional group such as methyltrimethoxysilane, ethyl trimethoxysilane, methyltriethoxysilane, phenyl trimethoxysilane, n-propyl trimethoxysilane, n-butyl trimethoxysilane, isobutyl trimethoxysilane and vinyl trimethoxysilane, but is not limited thereto.

Referring to FIG. 1 of the present disclosure, when methyltrimethoxysilane or ethyltrimethoxysilane is used as the organosilane compound, for example, the methoxy of $R_2$ in Chemical Formula 1 may be substituted with a hydroxy group by hydrolysis in a solvent.

The hydrolysis reaction can be described explicitly as follows. As the solvent, for example, when a mixed solvent of distilled water and ethanol are used, ethanol being unstable by water molecules reacts with oxygen of organosilane. As a result, the ethanol is stabilized again, and the silicon atom of the unstable organosilane and the OH$^-$ derived from the water molecule are bound to each other, so that the methoxy group of $R_2$ in Chemical Formula 1 is released and replaced with a hydroxyl group. Accordingly, the hydroxy group can be removed through the subsequent condensation reaction.

Specifically, the porous silica particles containing a hydrophilic group and the organosilane compound in which $R_2$ is substituted with hydrogen are reacted in the presence of a basic catalyst, resulting in the rapid condensation reaction. Thus, the hydrogen of $R_2$ of the organosilane compound is reacted with the hydrophilic group on the surface of the porous silica particles to generate $H_2O$. Then, the organosilane compound is attached to the surface of the silica particles, and the attached organosilane compound is connected to each other, thereby coating the surface of the silica particles.

Particularly, condensation between the starting materials can be promoted by proceeding hydrolysis in a liquid phase catalyst so that the condensation and the molecular weight can be increased.

According to an embodiment of the present disclosure, known bases may be used as a basic catalyst without limitation for the hydrolysis-condensation reaction. For example, the basic catalyst may be ammonia water ($NH_4OH$), but is not limited thereto.

According to an embodiment of the present disclosure, the basic catalyst may adjust the pH of the mixed solvent to be pH 10 to pH 14, preferably pH 11, but is not limited thereto.

The pH range from pH 10 to pH 14 is a pH range within a basic range in which condensation reaction can occur. It can be the range that suppresses the homogeneous nucleation of the coating molecules and causes only heterogeneous nucleation at the surface of conventional porous silicon particles. Accordingly, the pH of the mixed solvent is adjusted to the above range so as to inhibit the self-formation of particles of the organosilane compound used for the hydrophobic-coating on the surface of the porous silica particles in the present disclosure.

According to an embodiment of the present disclosure, after the step of reacting the porous silica particles containing the hydrophilic group with the organosilane compound under a basic catalyst, the step of adding an acidic solution to adjust the pH of the solution may be further included, but is not limited thereto.

According to an embodiment of the present disclosure, an acid which is known in the art for the hydrolysis-condensation reaction may be used as an acidic solution without limitation. For example, the acidic solution may be one selected from the group consisting of HCl, $H_2SO_4$, $HNO_3$ and combinations thereof, but is not limited thereto.

According to an embodiment of the present disclosure, the solvent can be adjusted to pH 5 to pH 8, preferably to pH 7, but is not limited thereto.

As described above, when the pH of the solvent is adjusted within the range of pH 5 to pH 8, the solvent can be neutralized to finish the condensation reaction.

According to an embodiment of the present disclosure, the step of drying the porous silica particle may be performed at 70° C. to 150° C., but is not limited thereto.

The second aspect of the present disclosure relates to a hydrophobic porous silica particle prepared by the above-described method, wherein at least 90% of the surface area of the porous silica particle is modified to be hydrophobic.

The second aspect of the present disclosure relates to a hydrophobic porous silica particle, in which at least 90% of the surface area is modified to be hydrophobic according to the first aspect of the present disclosure. Further detailed description that overlaps with the first aspect of the present disclosure will be excluded. However, although the further description is excluded, the description of the first aspect of the present disclosure may be applied equally to the second aspect of the present disclosure.

Hereinafter, the present disclosure is described in more detail with reference to the following examples. However, the following examples are for illustrative purposes only and are not intended to limit the scope of the present disclosure.

Example 1. Modification of Surface of Porous Silica Particles

In order to modify the surface of the porous silica particles to be hydrophobic, 100 g of porous silica particles and 40 g of organosilane compound, methyltrimethoxysilane (MTMS) or ethyltrimethoxysilane (ETMS) were added to a mixed solution of 300 ml of distilled water and 100 g of ethanol, and the mixtures were stirred for 30 minutes. As a catalyst, ammonia water was added to each stirred solution to adjust its pH to 11.

The solutions were further stirred for 6 hours and then adjusted to pH 7 with HCl.

The solutions were filtered to obtain porous silica particles, followed by washing and drying at 100° C. under a vacuum for one day to obtain porous silica particles whose surface was modified to have hydrophobicity.

Experiment Example 1. Evaluation of Hydrophobicity

The hydrophobic properties of the surface-modified hydrophobic porous silica particles by the organosilane compound prepared by the above Example 1 were evaluated. As a comparative example, poly (methyl methacrylate) (PMMA) was used, which is a microbead commonly used for exfoliating cosmetics. It was purchased from SUNJIN BEAUTY SCIENCE in South Korea (PMMA1 (SUNPMMA-P20 Lot: 15106001) and PMMA2 (SUNPMMA-COCO130 Lot: 15120110)).

Specifically, 2 g of hydrophobic porous silica particles having surface-modified with MTMS was added to 100 ml of water, and the mixture was stirred at 600 rpm for 30 seconds. 2 g of hydrophobic porous silica particles having surface-modified ETMS molecules was added to 100 ml of water, and the mixture was stirred at 600 rpm for 30 seconds. 2 g of PMMA commonly used in exfoliating cosmetics was added to 100 ml of water, and the mixture was stirred at 600 rpm for 30 seconds. After 10 minutes, the transparency of each solution was compared to confirm the hydrophobicity of each particle.

Figure 2:
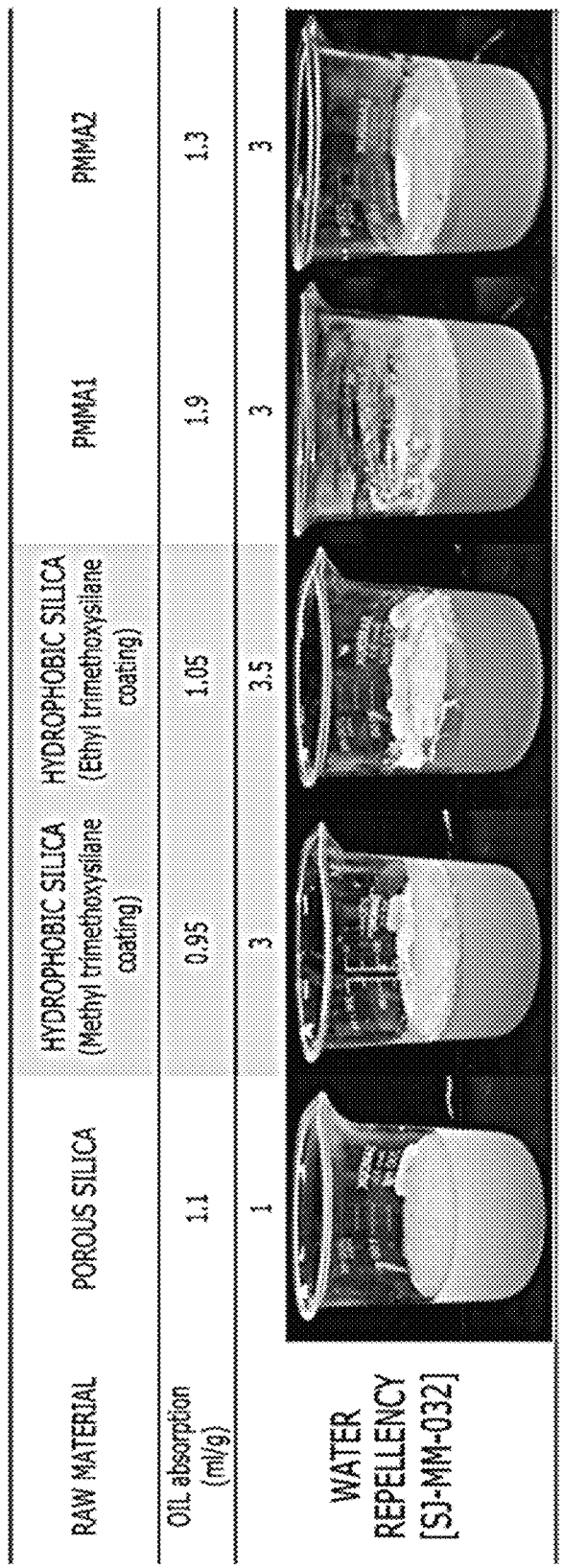
FIG. 2 shows the results of evaluating the hydrophobicity of the hydrophobic porous silica, according to an embodiment of the present disclosure.

As shown in FIG. 2, the results indicate that all of the hydrophobic surfaces-modified porous silica particles of the present disclosure exhibited water repellency and oil absorption sufficient to replace PMMA. Meanwhile, the hydrophobic surface-modified porous silica particles showed a smaller oil absorption than the non-surface-modified porous silica particles. This is because not only the outer part of the porous silica particles but also the inner pores are coated with the hydrophobic molecules, and the volume occupied by the pores is reduced. Therefore, it has been confirmed that the hydrophobic porous silica particles of the present disclosure can be applied to cosmetics that use conventional hydrophobic polymer beads.

Experiment Example 2. Analysis of Infrared Absorption

The functional groups of the hydrophobic porous silica particles having surface-modified with the organosilane compound prepared in Example 1 were confirmed by infrared absorption analysis.

Figure 3:
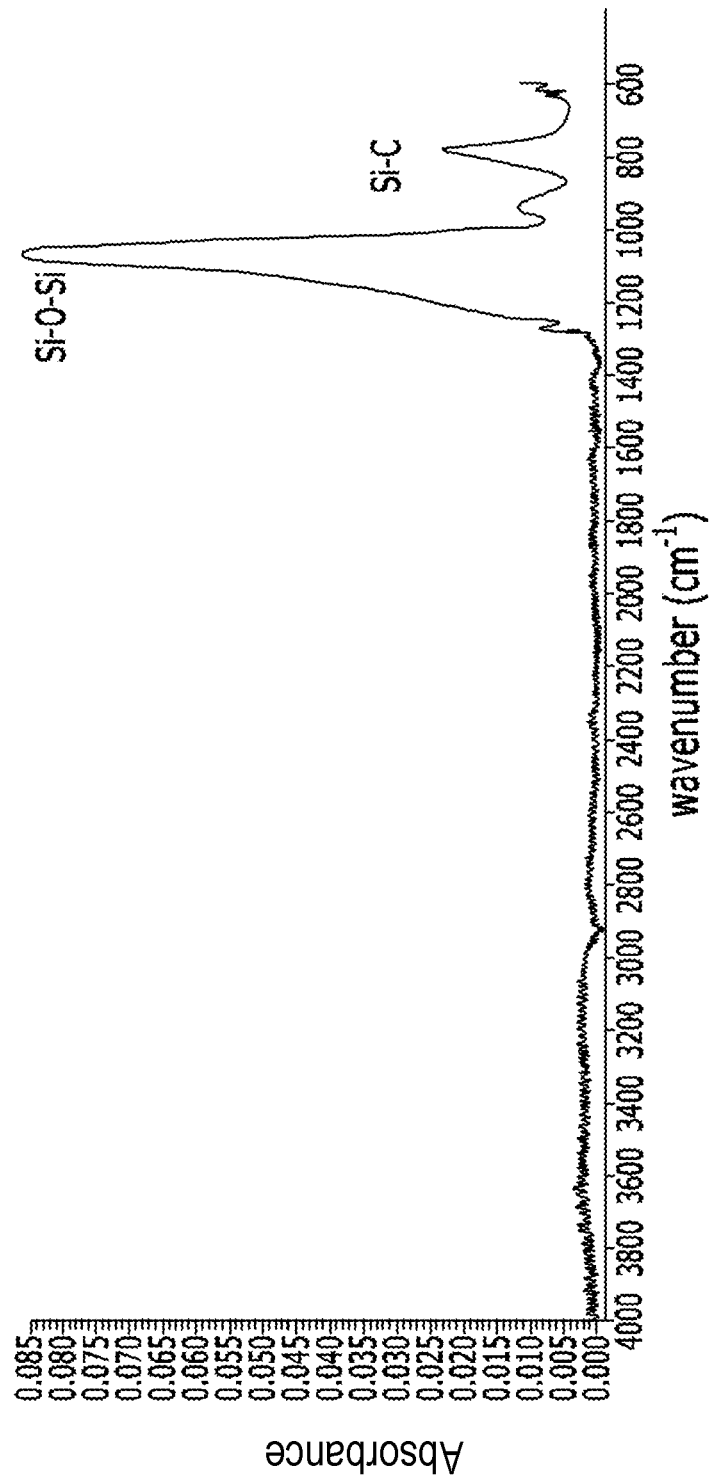
FIG. 3 shows the results of the infrared ray absorption of a surface-modified hydrophobic silica sphere using methyltrimethoxysilane (MTMS), according to an embodiment of the present disclosure.
Figure 4:
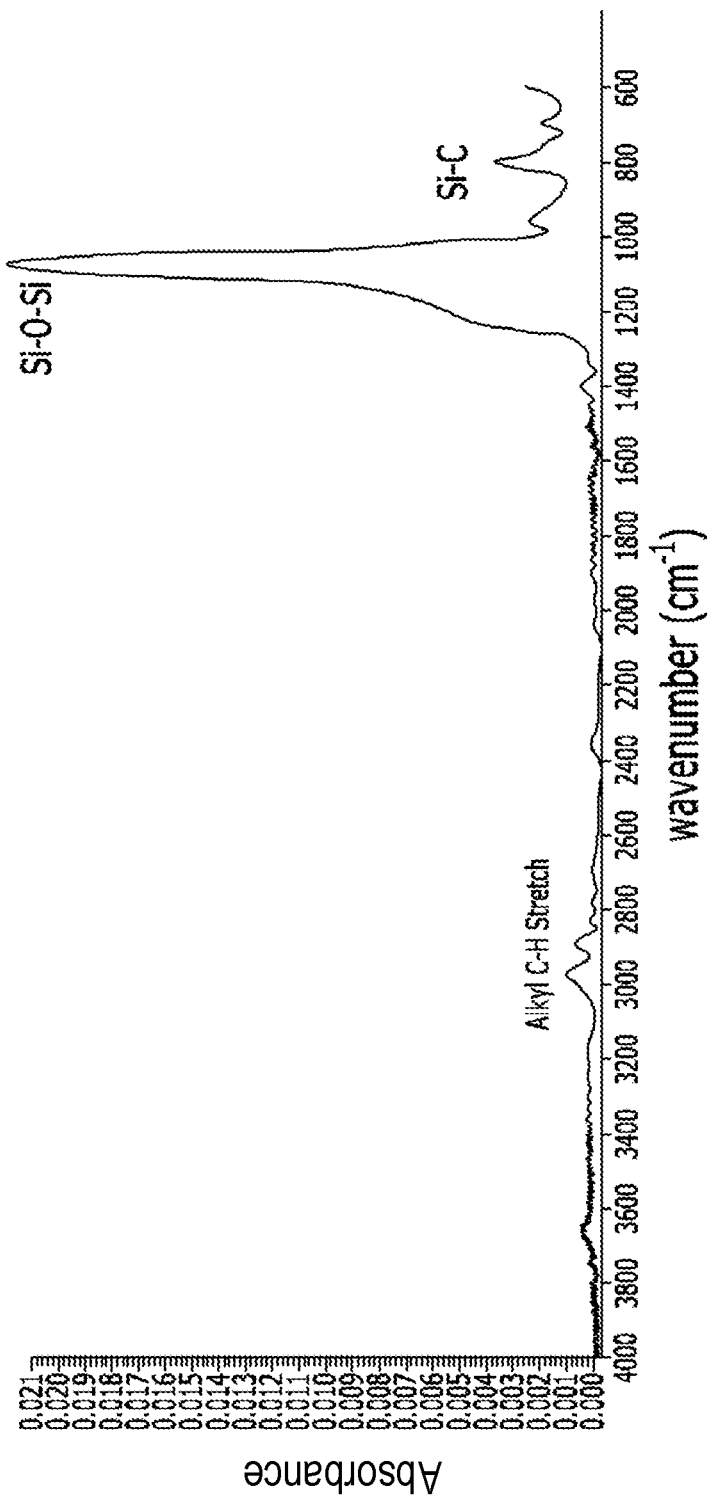
FIG. 4 shows the results of the infrared ray absorption of a surface-modified hydrophobic silica sphere using ethyltrimethoxysilane (ETMS), according to an embodiment of the present disclosure.

As shown in FIGS. 3 and 4, the results indicate that all of the hydrophobic surface-modified porous silica particles using MTMS and the hydrophobic surface-modified porous silica particles using ETMS showed high peaks at the wavelengths of 1200 to 1000, respectively. This peak indicates Si—O—Si. Particularly, a specific peak was identified at a wavelength of 800, indicating Si—C. Thus, it was confirmed that the surface of the porous silica particles of the present disclosure was modified to be hydrophobic.

It will be understood by those of ordinary skill in the art that the foregoing description of the present disclosure is for illustrative purposes and that various specific embodiments may be easily implemented without departing from the technical spirit or essential characteristics of the present disclosure.

It is, therefore, to be understood that the above-described embodiments are illustrative in all aspects and not restrictive. For example, each component described as a singular form may be distributed and implemented, and components described as being distributed may also be implemented in a combined form. The scope of the present disclosure is defined by the appended claims rather than the detailed description, and all changes or modifications derived from the meaning and scope of the claims and their equivalents should be construed as being included within the scope of the present disclosure.

What is claimed is:

1. A method of preparing hydrophobic porous silica, the method comprising:
   reacting a porous silica particle comprising a hydrophilic group in a solvent with an organosilane compound on a surface of the porous silica particle in the presence of a basic catalyst to form a mixture;

adding an acidic solution to adjust a pH of the mixture, the acidic solution being one selected from the group consisting of HCl, $H_2SO_4$, $HNO_3$ and combinations thereof; and drying the mixture comprising the porous silica particle in a vacuum to modify the surface of the porous silica particle to be hydrophobic.

2. The method according to claim 1, wherein the organosilane compound is hydrolyzed in the solvent.

3. The method according to claim 1, wherein the organosilane compound comprises a compound represented by the following Chemical Formula 1:

$$R_1\text{—}Si\text{—}(OR_2)_3 \qquad \text{[Chemical Formula 1]}$$

wherein $R_1$ is an alkyl group having C1 to C12, an alkenyl group having C2 to C10, a cycloalkyl group having C3 to C12 or an aryl group having C6 to C12, and $R_2$ is an alkyl group having C1 to C6.

4. The method according to claim 1, wherein the step of drying the porous silica particle in a vacuum is carried out at 70° C. to 150° C.

5. The method according to claim 1, wherein the solvent is one selected from the group consisting of distilled water, ethanol, methanol, isopropyl alcohol, n-propyl alcohol, butanol, and combinations thereof.

6. The method according to claim 1, wherein the basic catalyst is ammonia water ($NH_4OH$).

7. The method according to claim 1, wherein the pH of the mixture is adjusted to be from pH 10 to pH 14 by the basic catalyst.

8. The method according to claim 1, wherein the step of adding the acidic solution to adjust the pH of the mixture is such that the pH of the mixture is adjusted to be from pH 5 to pH 8.

9. The method according to claim 1, wherein the solvent is a mixture of distilled water and ethanol.

\* \* \* \* \*